United States Patent
Sun et al.

(10) Patent No.: US 11,384,109 B2
(45) Date of Patent: Jul. 12, 2022

(54) **METHOD FOR SEPARATING PHENOLIC ACID GLUCOSIDE COMPOUNDS FROM *DIAPHRAGMA JUGLANDIS FRUCTU***

(71) Applicant: Jiangnan University, Wuxi (CN)

(72) Inventors: Xiulan Sun, Wuxi (CN); Yida Xu, Wuxi (CN); Deping Xu, Wuxi (CN); Yinzhi Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/506,985

(22) Filed: Oct. 21, 2021

(65) Prior Publication Data

US 2022/0041639 A1 Feb. 10, 2022

Related U.S. Application Data

(63) Continuation of application No. PCT/CN2021/098138, filed on Jun. 3, 2021.

(30) Foreign Application Priority Data

Jun. 3, 2020 (CN) .......................... 202010502435.1

(51) Int. Cl.
*C07H 1/08* (2006.01)
*A61K 31/704* (2006.01)
*C07H 15/203* (2006.01)
*A61K 31/7034* (2006.01)
*A61K 36/52* (2006.01)

(52) U.S. Cl.
CPC ............. *C07H 1/08* (2013.01); *A61K 31/704* (2013.01); *A61K 31/7034* (2013.01); *A61K 36/52* (2013.01); *C07H 15/203* (2013.01); *A61K 2236/15* (2013.01); *A61K 2236/333* (2013.01); *A61K 2236/39* (2013.01)

(58) Field of Classification Search
None
See application file for complete search history.

(56) References Cited

FOREIGN PATENT DOCUMENTS

| CN | 101366827 A | 2/2009 |
|---|---|---|
| CN | 101611148 A | 12/2009 |
| CN | 104725520 A | 6/2015 |
| CN | 104961779 A | 10/2015 |
| CN | 105801634 A | 7/2016 |
| CN | 105801637 A | 7/2016 |
| CN | 105859805 A | 8/2016 |
| CN | 108997509 A | 12/2018 |
| CN | 110078654 A | 8/2019 |
| CN | 110302240 A | 10/2019 |
| CN | 111704639 A | 9/2020 |
| JP | 2005200319 A | 7/2005 |

OTHER PUBLICATIONS

"MCI(R) GEL" product brochure published by Mitsubishi chemical, technical information 2008-2009 (Year: 2008).*
Wang et al., "Chemical Constituents of the Ethyl Acetate Extract from Diaphragma juglandis Fructus and Their Inhibitory Activity on Nitric Oxide Production In Vitro" Molecules vol. 23 doi:10.3390/molecules23010072 (Year: 2018).*
Yang et al., "Rapid chemical profiling of saponins in the flower buds of Panax notoginseng by integrating MCI gel column chromatography and liquid chromatography/mass spectrometry analysis" Food Chemistry vol. 139 pp. 762-769 DOI: 10.1016/j.foodchem.2013.01.051 (Year: 2013).*
Pei et al., "Isolation of high-purity peptide Val-Val-Tyr-Pro from Globin Peptide using MCI gel column combined with high-speed counter-current chromatography" Journal of Separation Science vol. 41 pp. 4559-4566 DOI: 10.1002/jssc.201800972 (Year: 2018).*
Fu et al., "A Novel and Effective Chromatographic Approach to the Separation of Isoflavone Derivatives from Pueraria lobata" vol. 20 pp. 4238-4253 DOI: 10.3390/molecules20034238 (Year: 2015).*
Xianhua Meng, et. al. "Phenolic chemical constituents of Zanthoxylum schinifolium pericarps and their anti-oxidative effects." Chinese Traditional and Herber Drugs. Issue 51 vol. 8, Apr. 2020.
Anis Ben Hsouna, et. al. "Antioxidant constituents from Lawsonia inermis leaves: isolation, structure elucidation and antioxidative capacity." Food Chemistry, 125, 2011, 193-200.

* cited by examiner

*Primary Examiner* — Eric Olson
(74) *Attorney, Agent, or Firm* — IPro, PLLC

(57) ABSTRACT

The disclosure discloses a method for separating phenolic acid glucoside compounds from *Diaphragma juglandis Fructus*, belonging to the technical field of food. The method includes the following steps: (1) extraction: crushing *Diaphragma juglandis Fructus*, and then extracting by using ethanol to obtain walnut ethanol extract; and (2) separation: performing column chromatography on the walnut ethanol extract obtained in step (1), sequentially eluting by using ethanol of different concentrations, purifying and eluting repeatedly, and performing separation to obtain phenolic acid glucoside compounds. The phenolic acid glucoside compounds are 2-hydroxyl-5-methoxylphenyl-O-β-D-glucopyranoside, 6-hydroxylnaphthyl-1,2-di-O-β-D-glucopyranoside and 2,6-dihydroxynaphthyl-O-β-D-glucopyranoside. Pharmacological experiments confirm that the three compounds have good antioxidant activity.

5 Claims, 11 Drawing Sheets

METHOD FOR SEPARATING PHENOLIC ACID GLUCOSIDE COMPOUNDS FROM *DIAPHRAGMA JUGLANDIS FRUCTU*

TECHNICAL FIELD

The disclosure relates a method for separating phenolic acid glucoside compounds from *Diaphragma juglandis Fructus*, belonging to the technical field of food.

BACKGROUND

Walnut is the mature seed of *Juglans regial* L., which is rich in unsaturated fatty acids, is known as the "king of woody oil plants", and has the functions of improving cerebral ischemia, resisting fatigue and improving memory. However, the comprehensive utilization and development of walnut products, such as *Diaphragma juglandis Fructus* in walnut byproducts, are still not enough. At present, the literature report on *Diaphragma juglandis Fructus* shows that *Diaphragma juglandis Fructus* contains flavonoid compounds such as quercetin and catechin, volatile substances such as menthol and cedrol, and phenolic acid compounds such as gallic acid, and has many active functions of resisting bacteria, resisting oxidation, reducing blood sugar, inhibiting brain function decline, resisting tumor and so on. However, the specific compounds and their corresponding bioactive functions are not clear, which need further research and confirmation. In order to improve the comprehensive utilization of walnut byproducts and enhance the added value of walnut products, it is necessary to clarify the functional components in *Diaphragma juglandis Fructus*.

SUMMARY

The disclosure separates and obtains three phenolic acid glucoside compounds from *Diaphragma juglandis Fructus* for the first time, which are respectively 2-hydroxyl-5-methoxylphenyl-O-β-D-glucopyranoside, 6-hydroxylnaphthyl-1,2-di-O-β-D-glucopyranoside and 2,6-dihydroxynaphthyl-O-β-D-glucopyranoside. Pharmacological experiments confirm that they have good antioxidant activity.

The disclosure discloses a method for separating phenolic acid glucoside compounds from *Diaphragma juglandis Fructus*. The method includes the following steps:

(1) extraction: crushing *Diaphragma juglandis Fructus*, and then extracting by using ethanol to obtain walnut ethanol extract; and (2) separation: performing column chromatography to the walnut ethanol extract obtained in step (1), sequentially eluting by using ethanol of different concentrations, purifying and eluting repeatedly, and performing separation to obtain phenolic acid glucoside compounds. The phenolic acid glucoside compounds are 2-hydroxyl-5-methoxylphenyl-O-β-D-glucopyranoside, 6-hydroxylnaphthyl-1,2-di-O-β-D-glucopyranoside and 2,6-dihydroxynaphthyl-O-β-D-glucopyranoside.

In an implementation of the disclosure, the structural formula of the 2-hydroxyl-5-methoxylphenyl-O-β-D-glucopyranoside is:

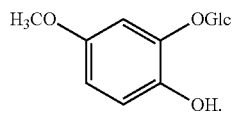

In an embodiment of the disclosure, the structural formula of the 6-hydroxylnaphthyl-1,2-di-O-β-D-glucopyranoside is:

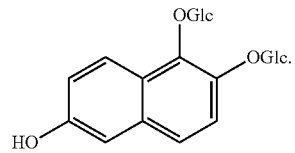

In an embodiment of the disclosure, the structural formula of the 2,6-dihydroxynaphthyl-O-β-D-glucopyranoside is:

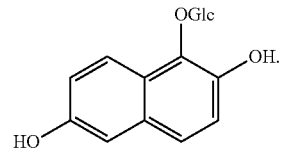

In an embodiment of the disclosure, a material-liquid ratio of *Diaphragma juglandis Fructus* to ethanol solution in step (1) is 1:(10-20) (M/V, g/mL).

In an embodiment of the disclosure, in step (1), extraction is to crush *Diaphragma juglandis Fructus*, then add 75% ethanol according to a material-liquid ratio of 1:(10-20) (M/V, g/mL), stir the mixture for extraction at 40-70° C. for 2-5 h, and filter to take supernatant, repeat the operation three times, performing reduced-pressure concentration on the supernatant obtained three times, and remove ethanol to obtain the walnut ethanol extract.

In an embodiment of the disclosure, step (2) is putting the walnut ethanol extract obtained in step (1) into an MCI GEL reverse phase column, sequentially eluting by using deionized water, 30% ethanol, 50% ethanol and 70% ethanol, collecting and then combining a water elution fraction and a 30% ethanol elution fraction, performing reduced-pressure concentration, putting a sample into an MCI GEL reverse phase column, sequentially performing gradient elution by using deionized water, 10% ethanol, 20% ethanol, 30% ethanol and 50% ethanol, collecting a 10% ethanol elution fraction, performing reduced-pressure concentration, then putting a sample into an ODS column, sequentially eluting by using deionized water, 5% ethanol solution, 10% ethanol solution and 20% ethanol solution, collecting the eluent, then purifying and eluting repeatedly, and performing separation to obtain phenolic acid glucoside compounds.

The disclosure discloses application of a phenolic acid glucoside compound to preparation of drugs and healthcare products for preventing or treating oxidative stress induced diseases. The phenolic acid glucoside compound is 2-hydroxyl-5-methoxylphenyl-O-β-D-glucopyranoside, 6-hydroxylnaphthyl-1,2-di-O-β-D-glucopyranoside or 2,6-dihydroxynaphthyl-O-β-D-glucopyranoside.

In an embodiment of the disclosure, the oxidative stress induced disease is chronic obstructive pulmonary disease, respiratory tract inflammation, skin lesion, diabetes, neurodegenerative disease or tumor disease.

In an embodiment of the disclosure, the phenolic acid glucoside compound is 2-hydroxyl-5-methoxylphenyl-O-β-D-glucopyranoside, the structural formula of which is:

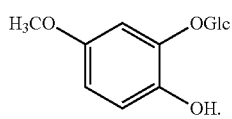

In an embodiment of the disclosure, the phenolic acid glucoside compound is 6-hydroxylnaphthyl-1,2-di-O-β-D-glucopyranoside, the structural formula of which is:

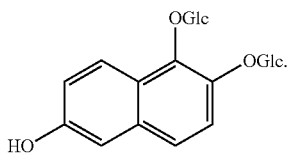

In an embodiment of the disclosure, the phenolic acid glucoside compound is 2,6-dihydroxynaphthyl-O-β-D-glucopyranoside, the structural formula of which is:

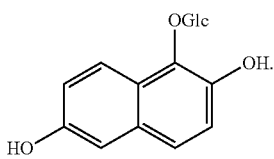

In an embodiment of the disclosure, the application is application to improve the superoxide dismutase (SOD) activity and reduce the MDA level of liver.

The disclosure discloses a composition having a treatment or healthcare function on oxidative stress related diseases. The active component in the composition is a phenolic acid glucoside compound. The composition includes one or more of 2-hydroxyl-5-methoxylphenyl-O-β-D-glucopyranoside, 6-hydroxylnaphthyl-1,2-di-O-β-D-glucopyranoside and 2,6-dihydroxynaphthyl-O-β-D-glucopyranoside.

In an embodiment of the disclosure, the composition further includes a carrier and/or an excipient.

In an embodiment of the disclosure, the dosage form of the composition is any one dosage form recognized in medicine, and the dosage form includes powder, tablet, injection, oral liquid or injection liquid.

The disclosure further discloses application of a phenolic acid glucoside compound to preparation of food or cosmetic products having an antioxidant function. The phenolic acid glucoside compound is 2-hydroxyl-5-methoxylphenyl-O-β-D-glucopyranoside, 6-hydroxylnaphthyl-1,2-di-O-β-D-glucopyranoside or 2,6-dihydroxynaphthyl-O-β-D-glucopyranoside.

The disclosure has the following beneficial effects:

In the research process of *Diaphragma juglandis Fructus* extract, we discovery three phenolic acid glucosides in *Diaphragma juglandis Fructus* extract for the first time, and provide a method for preparing the three compounds from walnut. Pharmacological experiments confirm that the three compounds can improve the SOD activity and reduce the MDA level, and have good antioxidant activity.

DETAILED DESCRIPTION

Figure 1:
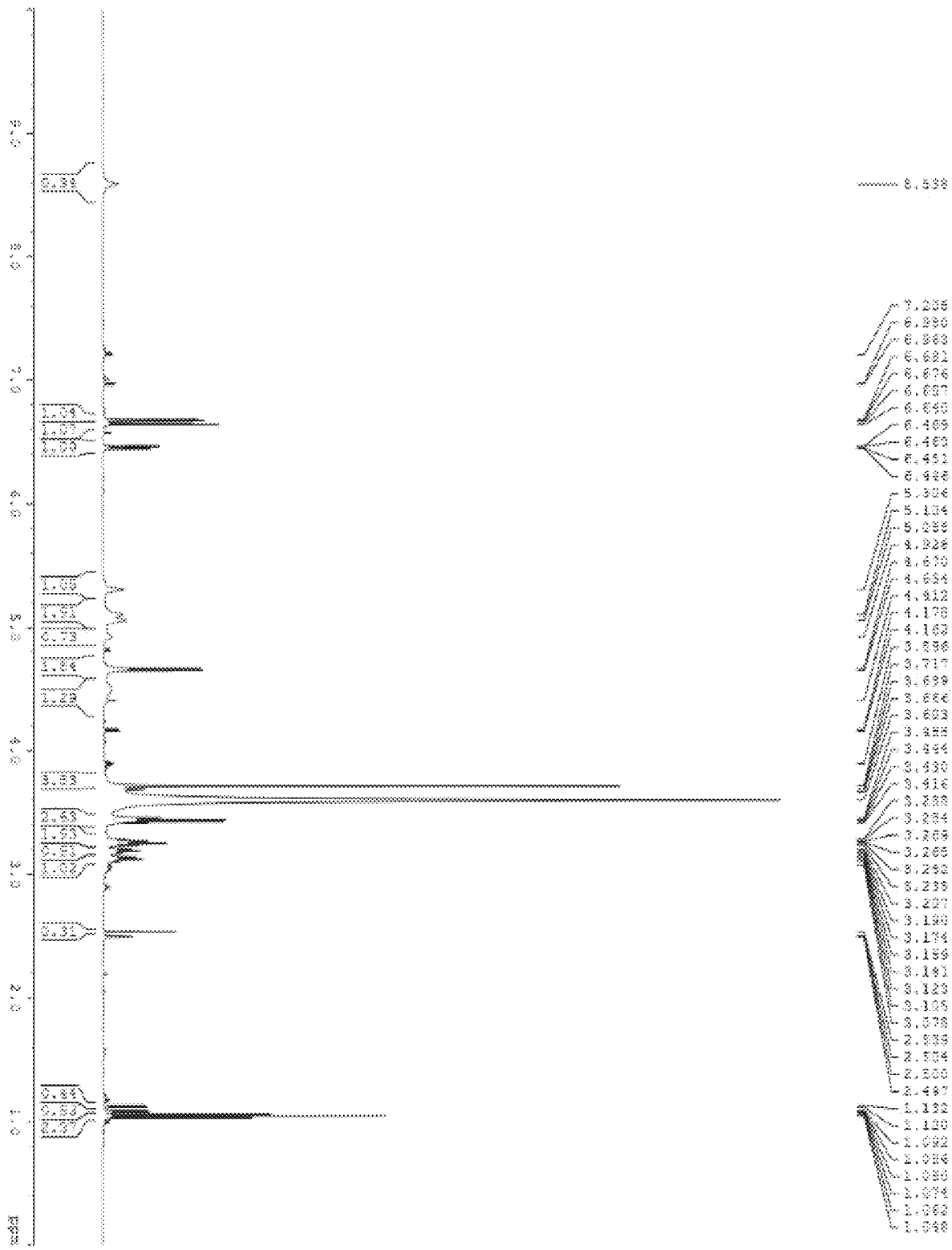
FIG. 1 is a $^1$H-NMR spectrogram of Compound 1.

The preferred examples of the disclosure will be described below. It should be understood that the examples are intended to better explain the disclosure and are not used to limit the disclosure.

Example 1

A method for extracting three phenolic acid glucoside compounds from *Juglans regial* L. mature seeds specifically included the following steps:

*Diaphragma juglandis Fructus* was crushed, then 75% ethanol was added according to a material-liquid ratio of 1:15 (M/V), the mixture was stirred for extraction at 50° C. for 3 h, and filtered to take supernatant, and the operation was repeated three times. Reduced-pressure concentration was performed on the supernatant obtained three times, and ethanol was removed to obtain the walnut ethanol extract. The walnut ethanol extract was put into an MCI reverse phase column, eluted sequentially by using deionized water, 30% ethanol, 50% ethanol and 70% ethanol, a water elution fraction and a 30% ethanol elution fraction were collected and then combined, reduced-pressure concentration was performed, a sample was loaded into an MCI GEL reverse phase column, gradient eluted sequentially by using deionized water, 10% ethanol, 20% ethanol, 30% ethanol and 50% ethanol, a 10% ethanol elution fraction was collected, reduced-pressure concentration was performed, then a sample was loaded into an ODS column, and eluted sequentially by using deionized water, 5% ethanol solution, 10% ethanol solution and 20% ethanol solution, the eluent was collected, then purification and elution were performed repeatedly, and separation was performed to obtain three phenolic acid glucoside compounds, which were respectively 2-hydroxyl-5-methoxylphenyl-O-β-D-glucopyranoside (Compound 1), 6-hydroxylnaphthyl-1,2-di-O-β-D-glucopyranoside (Compound 2) and 2,6-dihydroxynaphthyl-O-β-D-glucopyranoside (Compound 3). As measured by HPLC, the yields of the three compounds were 92%, 90% and 93% respectively, and the purity was 97.8%, 98.0% and 98.1% respectively.

Example 2

A method for extracting three compounds from walnut specifically includes the following steps:

*Diaphragma juglandis Fructus* was crushed, then 75% ethanol was added according to a material-liquid ratio of 1:10 (M/V), the mixture was stirred for extraction at 40° C. for 5 h, and filtered to take supernatant, and the operation was repeated three times. Reduced-pressure concentration was performed to the supernatant obtained three times, and ethanol was removed to obtain the walnut ethanol extract. The walnut ethanol extract was put into an MCI GEL reverse phase column, and eluted sequentially by using deionized water, 30% ethanol, 50% ethanol and 70% ethanol, a water elution fraction and a 30% ethanol elution fraction were collected and then combined, reduced-pressure concentration was performed, a sample was loaded into an MCI GEL reverse phase column, and gradient eluted sequentially by using deionized water, 10% ethanol, 20% ethanol, 30% ethanol and 50% ethanol, a 10% ethanol elution fraction was collected, reduced-pressure concentration was performed, then a sample was loaded into an ODS column, and eluted sequentially by using deionized water, 5% ethanol solution, 10% ethanol solution and 20% ethanol solution, the eluent was collected, then purification and elution were performed repeatedly, and separation was performed to obtain three new compounds, which were respectively 2-hydroxyl-5-methoxylphenyl-O-β-D-glucopyranoside (compound 1), 6-hydroxylnaphthyl-1,2-di-O-β-D-glucopyranoside (compound 2) and 2,6-dihydroxynaphthyl-O-β-D-glucopyranoside (compound 3). As measured by HPLC, the yields of the three compounds were 90%, 86% and 90% respectively, and the purity was 98.0%, 98.1% and 98.1% respectively.

Example 3

A method for extracting three compounds from walnut specifically includes the following steps:

*Diaphragma juglandis Fructus* was crushed, then 75% ethanol was added according to a material-liquid ratio of 1:20 (M/V), the mixture was stirred for extraction at 70° C. for 2 h, and filtered to take supernatant, and the operation was repeated three times. Reduced-pressure concentration was performed on the supernatant obtained three times, and ethanol was removed to obtain the walnut ethanol extract. The walnut ethanol extract was loaded into an MCI GEL reverse phase column, and eluted sequentially by using deionized water, 30% ethanol, 50% ethanol and 70% ethanol, a water elution fraction and a 30% ethanol elution fraction were collected and then combined, reduced-pressure concentration was performed, a sample was loaded into an MCI GEL reverse phase column, and gradient eluted sequentially by using deionized water, 10% ethanol, 20% ethanol, 30% ethanol and 50% ethanol, a 10% ethanol elution fraction was collected, reduced-pressure concentration was performed, then a sample was loaded into an ODS column, and eluted sequentially by using deionized water, 5% ethanol solution, 10% ethanol solution and 20% ethanol solution, the eluent was collected, then purification and elution were performed repeatedly, and separation was performed to obtain three new compounds, which were respectively 2-hydroxyl-5-methoxylphenyl-O-β-D-glucopyranoside (compound 1), 6-hydroxylnaphthyl-1,2-di-O-β-D-glucopyranoside (compound 2) and 2,6-dihydroxynaphthyl-O-β-D-glucopyranoside (compound 3). As measured by HPLC, the yields of the three compounds were 93%, 92% and 93.5% respectively, and the purity was 97.2%, 97.7% and 97.8% respectively.

Example 4

The disclosure provides structure analysis steps of the three new compounds, which are specifically as follows:

Compound 1 is a yellow amorphous powder, soluble in water, ethanol and the like, and insoluble in chloroform.

A $^1$H-NMR spectrogram of this compound is as shown in FIG. 1. From FIG. 1, it can be seen that there is one proton signal respectively at δ 6.46, δ 6.64 and δ 6.68, which are 3 hydrogens (Hs) on the same benzene ring. From the coupling constant, the 3 Hs are distributed in the ortho and meta sites on the benzene ring. There is a proton signal of glucose terminal group at δ5.31, the glucose is of a β configuration, and δ 3.01 to δ 3.21 are other proton signals on the glucose.

Figure 2:
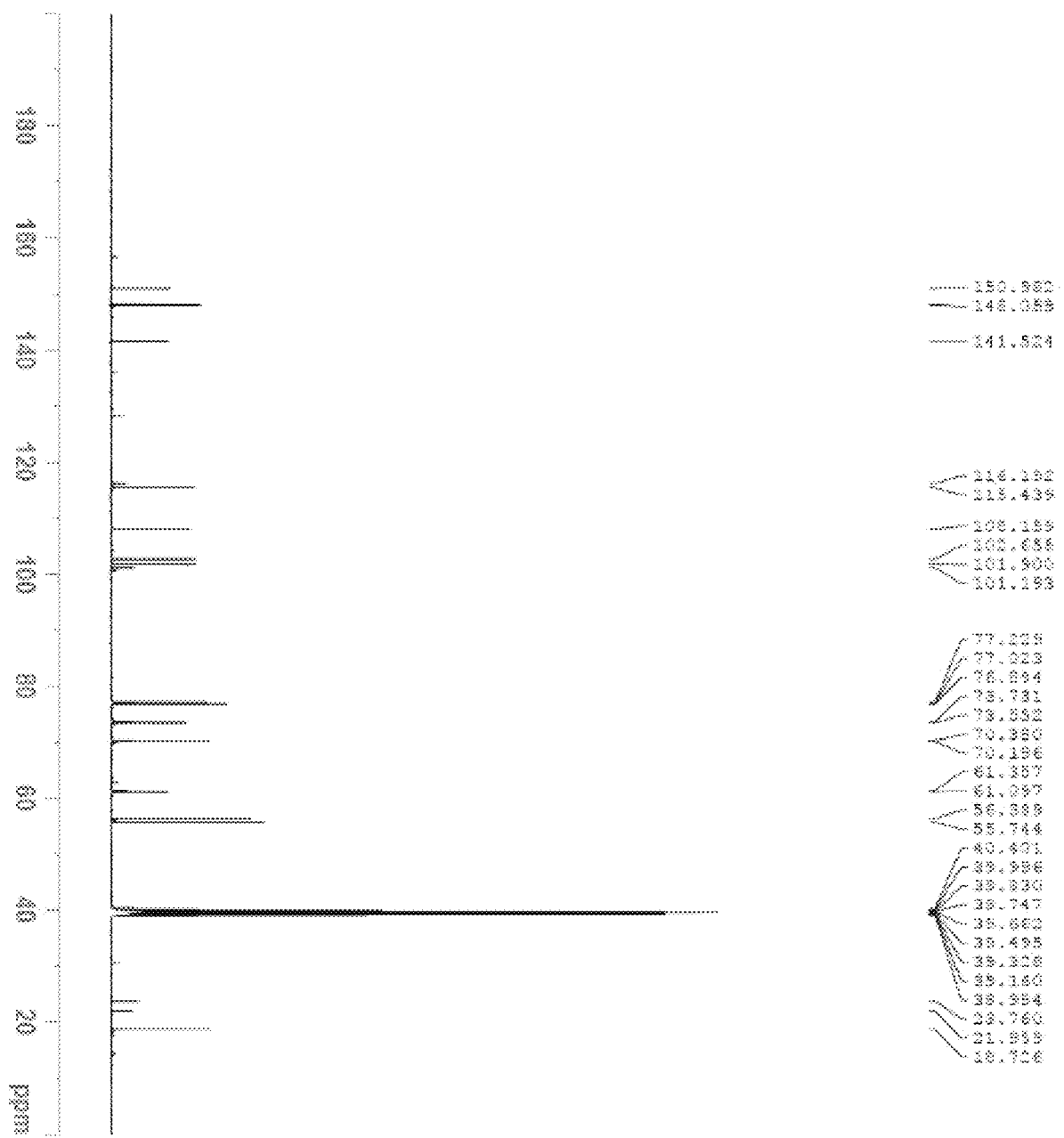
FIG. 2 is a $^{13}$C-NMR spectrogram of Compound 1.

A $^{13}$C-NMR spectrogram of Compound 1 is as shown in FIG. 2. From FIG. 2, it can be seen that Compound 1 has 13 carbons, of which 6 are carbons in glucose. Δ 141.52, δ 148.06 and δ 150.98 are oxycarbon signals on the benzene ring, δ 102.00, δ 108.16 and δ 115.44 are —CH— signals on the benzene ring, and δ 55.74 is a methoxy group signal on the benzene ring.

Figure 3:
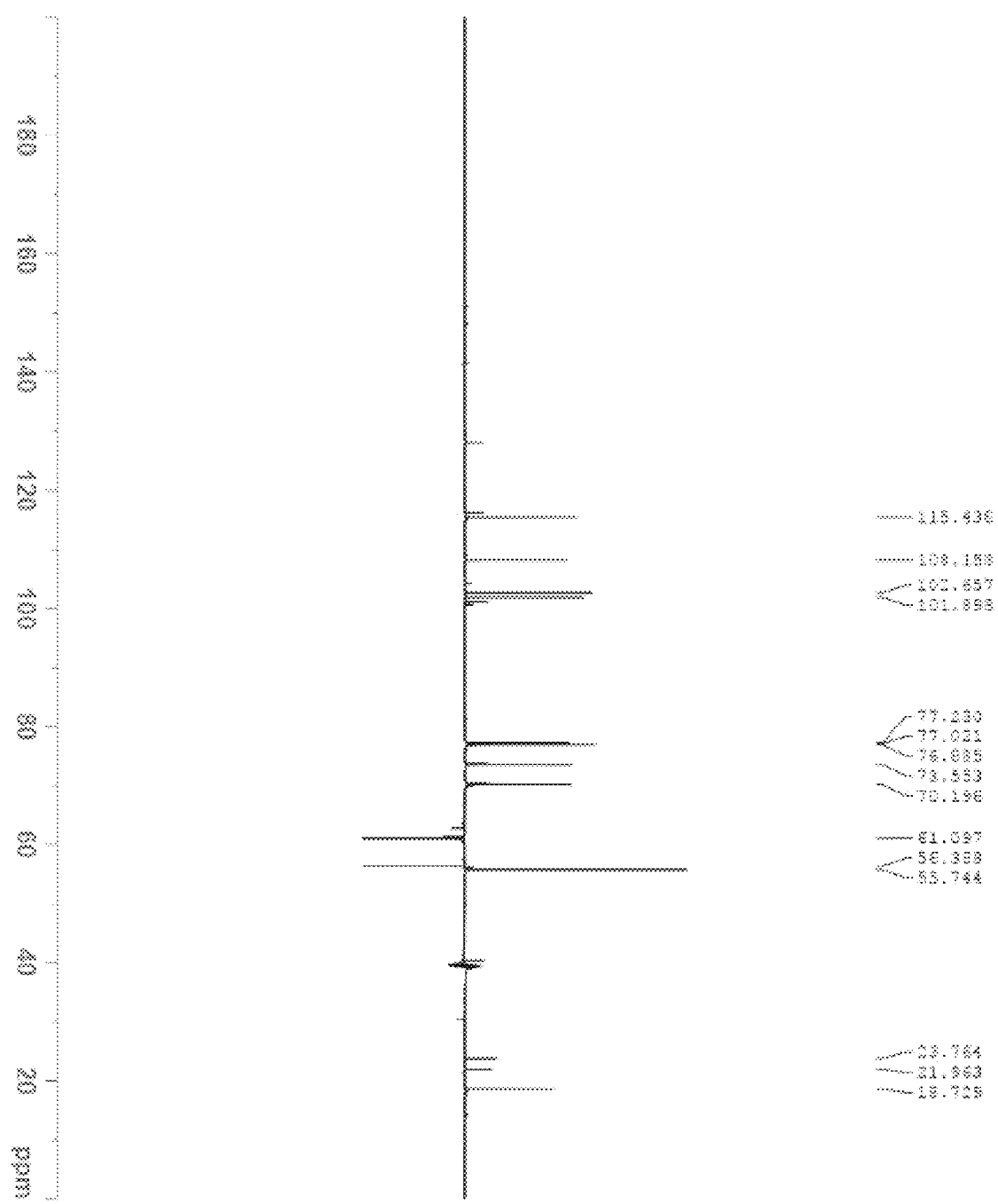
FIG. 3 is a $^{135}$DEPT-NMR spectrogram of Compound 1.
Figure 4:
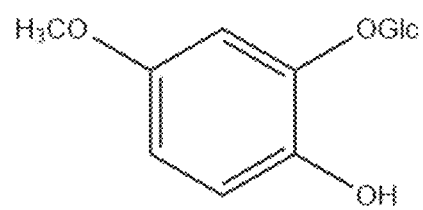
FIG. 4 is a structural formula of Compound 1.

By combining the $^1$H-NMR spectrum, the $^{13}$C-NMR spectrum and the $^{135}$DEPT-NMR spectrum (FIG. 3) data of this compound and with reference to the literature, it can be determined that this compound is 2-hydroxyl-5-methoxylphenyl-O-β-D-glucopyranoside, the structural formula of which is as shown in FIG. 4.

Compound 2 is white powder, soluble in water, ethanol and the like, and insoluble in chloroform.

Figure 5:
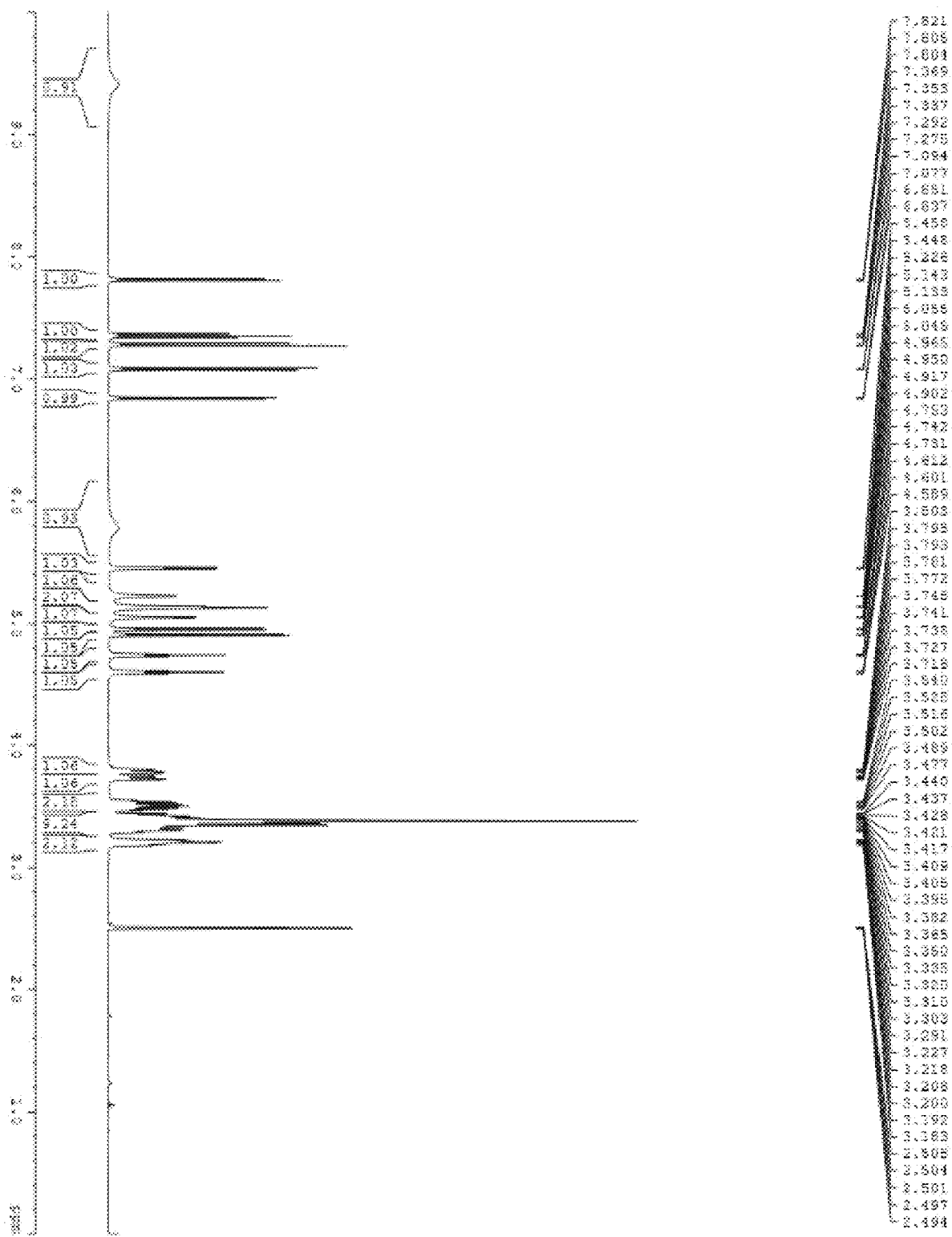
FIG. 5 is a $^1$H-NMR spectrogram of Compound 2.

A $^1$H-NMR spectrogram of this compound is as shown in FIG. 5. From FIG. 5, it can be seen that there is a proton signal respectively at δ 6.84 and δ 7.01, which is a hydrogen on an ortho carbon of a carbon linked to a hydroxyl group. There are two glucose terminal proton signals at δ 5.45, the two glucoses are of a β configuration, and the two protons at the 6' site of the glucose are other proton signals on the glucose respectively at δ 3.50 and δ 3.54, and δ 3.18 to δ 3.44.

Figure 6:
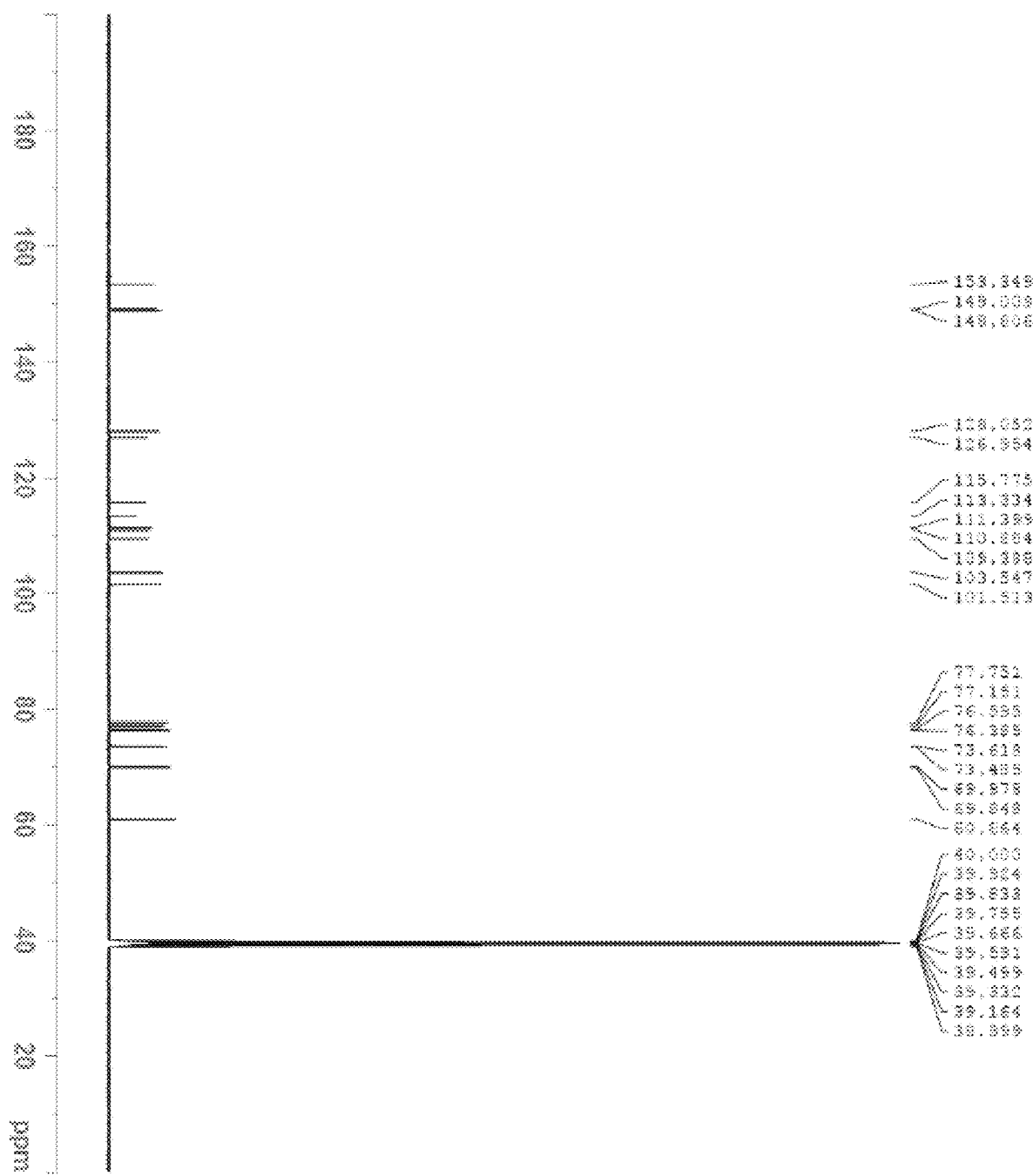
FIG. 6 is a $^{13}$C-NMR spectrogram of Compound 2.

A $^{13}$C-NMR spectrogram of this compound is as shown in FIG. 6. From FIG. 6, it can be seen that compound 2 totally has 22 carbons, of which 12 carbons are carbons in glucose. δ 148.81, δ 149.00 and δ 153.35 are oxycarbon signals on the naphthalene ring, δ 126.96 and δ 128.05 are carbon signals at the junction of two benzene rings, and δ 109.39 to δ 115.78 are —CH— signals on the naphthalene ring.

Figure 7:
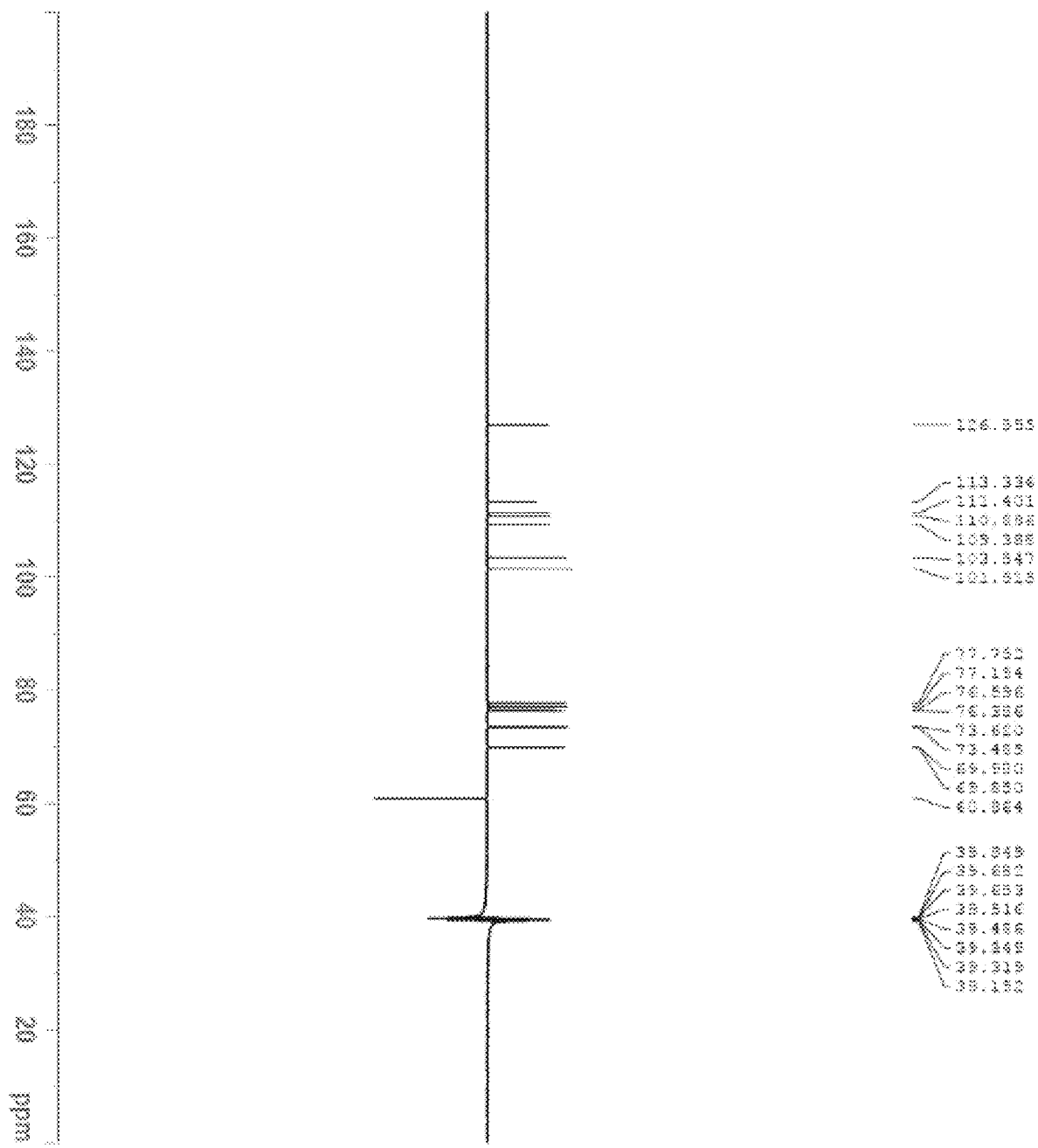
FIG. 7 is a $^{135}$DEPT-NMR spectrogram of Compound 2.
Figure 8:
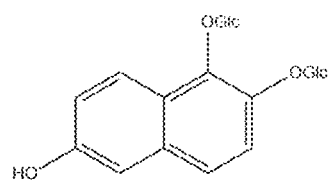
FIG. 8 is a structural formula of Compound 2.

According to the $^1$H-NMR spectrum, the $^{13}$C-NMR spectrum and the $^{135}$DEPT-NMR spectrum (FIG. 7) data of Compound 2 and with reference to the literature, it can be determined that this compound is 6-hydroxylnaphthyl-1,2-di-O-β-D-glucopyranoside, the structural formula of which is as shown in FIG. 8.

Compound 3 is brown amorphous powder, soluble in water, ethanol and the like, and insoluble in chloroform.

Figure 9:
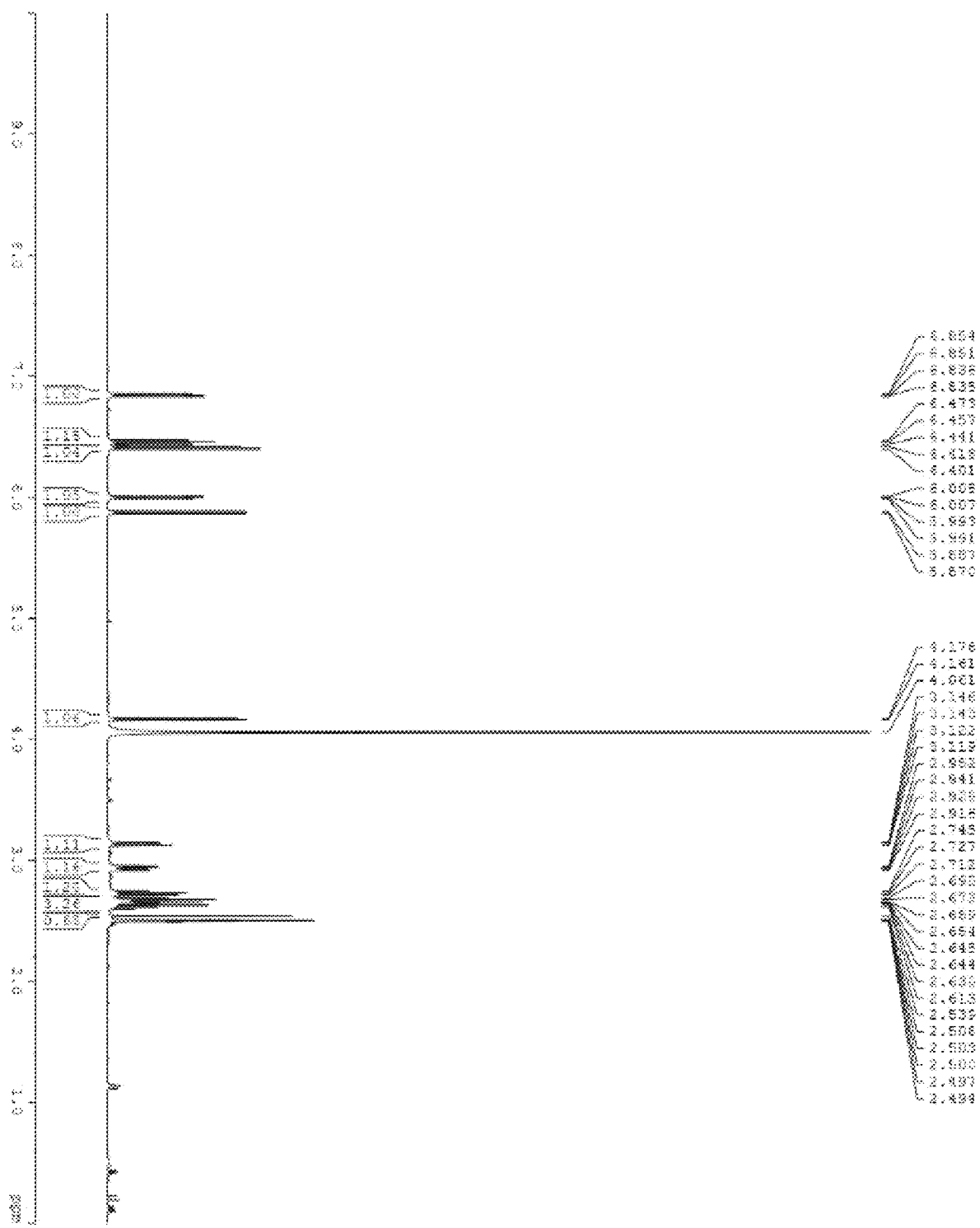
FIG. 9 is a $^1$H-NMR spectrogram of Compound 3.

A $^1$H-NMR spectrogram of this compound is as shown in FIG. 9. From FIG. 9, it can be seen that δ 6.00, δ 6.40, δ 6.46, δ 6.84 and δ 6.85 are aromatic hydrogen proton signals on the naphthalene ring. There is a glucose terminal proton signal at δ 5.87, and the glucose is of a β configuration.

Figure 10:
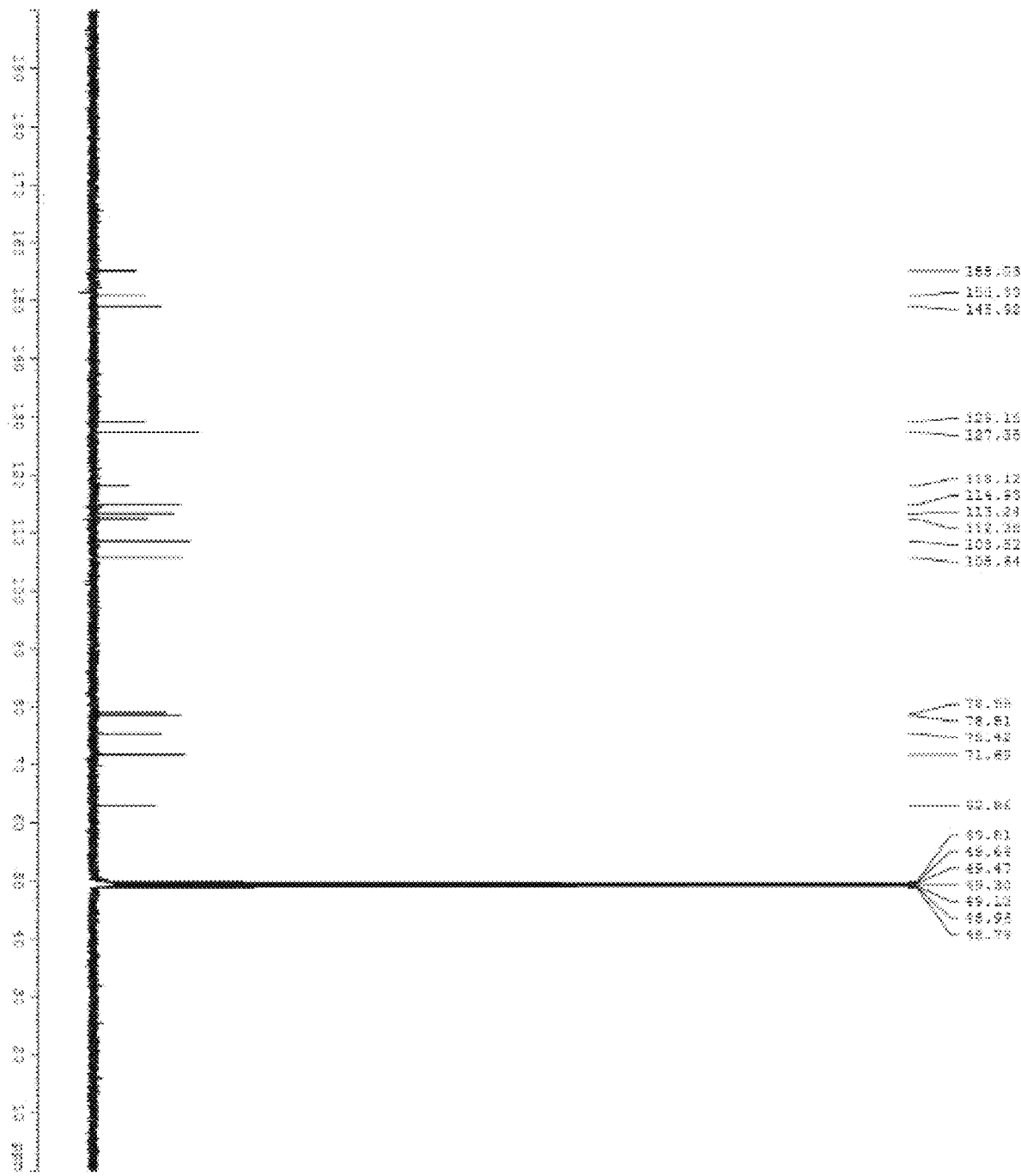
FIG. 10 is a $^{13}$C-NMR spectrogram of Compound 3.

A $^{13}$C-NMR spectrogram of this compound is as shown in FIG. 10. From FIG. 10, it can be seen that Compound 3 totally has 16 carbons, of which 6 carbons are carbons in glucose. δ 148.92, δ 150.83 and δ 155.03 are oxycarbon signals on the naphthalene ring, δ 108.52 to δ 129.15 are other carbon signals on the naphthalene ring, and δ 62.86 to δ 105.64 are carbon signal on the glycosyl group.

Figure 11:
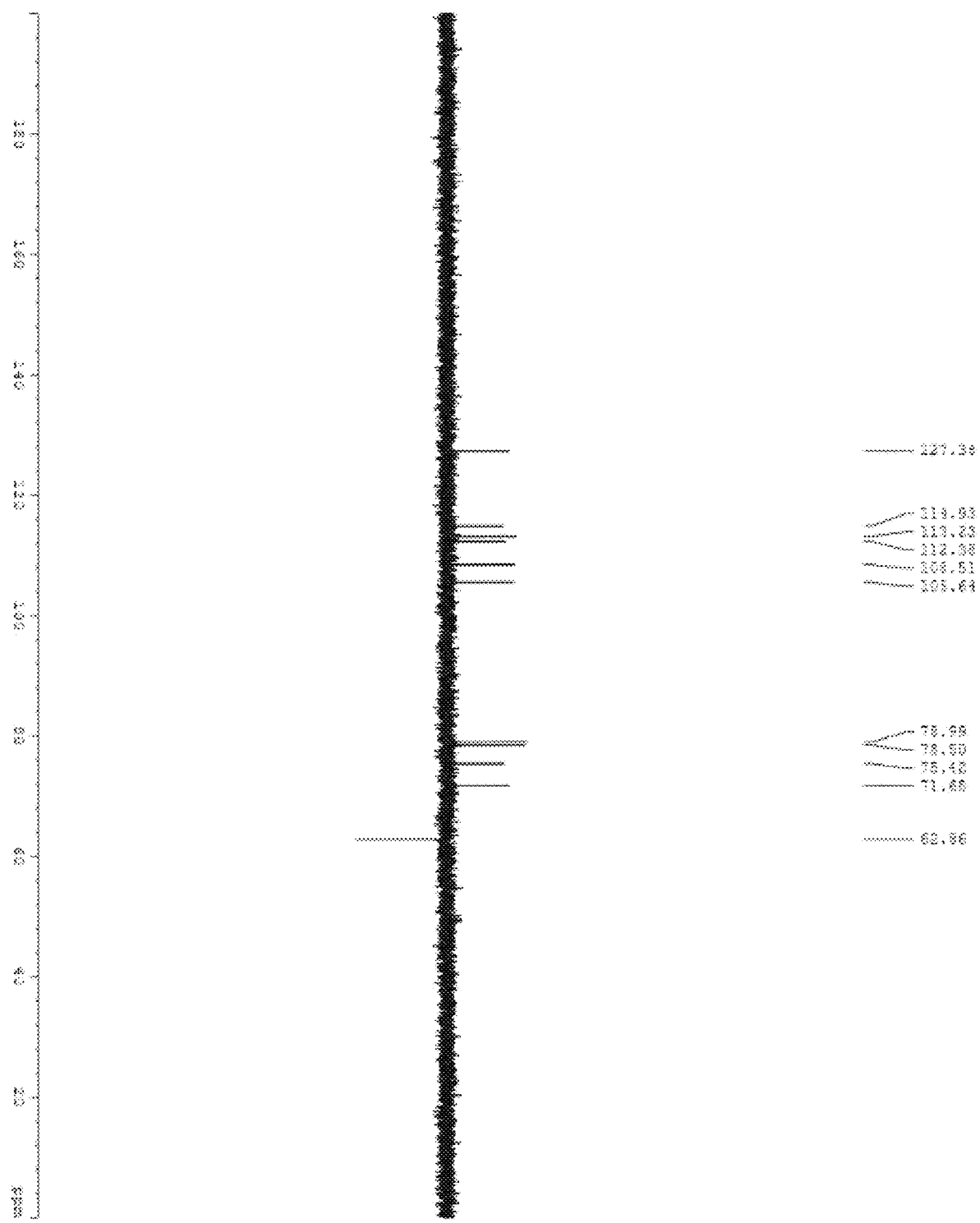
FIG. 11 is a $^{135}$DEPT-NMR spectrogram of Compound 3.
Figure 12:
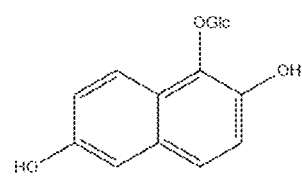
FIG. 12 is a structural formula of Compound 3.

According to the $^1$H-NMR spectrum, the $^{13}$C-NMR spectrum and the $^{135}$DEPT-NMR spectrum (FIG. 11) data of Compound 3 and with reference to the literature, it can be determined that this compound is 2,6-dihydroxynaphthyl-O-β-D-glucopyranoside, the structural formula of which is as shown in FIG. 12.

Example 5: Antioxidant Effects of Three Compounds

Materials and Methods

1 Materials 1.1 Animals: ICR mice, 6 weeks old, 20-25 g, SPF grade, purchased from Shanghai Slack Experimental Animal Co., Ltd.

1.2 Reagents: D-galactose, purchased from Sigma, USA; malondialdehyde (MDA) kit, purchased from Nanjing Jiancheng Bioengineering Institute; superoxide dismutase (SOD) kit, purchased from Shanghai Aisalai Eliza Biotechnology Co., Ltd.

2 Experimental Methods 2.1 Animal grouping and administration: after one week of adaptive feeding, mice were randomly divided into 5 groups, 10 mice each group. The administration group was gavaged with Compounds 1-3, 500 mg/kg per compound. The blank group and aging model group were gavaged with equal volume of normal saline for 6 weeks. At the same time, 150 mg/kg D-galactose was injected subcutaneously into the aging model group and the administration group respectively to establish a subacute aging model of mice. The blank control group was injected with equal volume of normal saline for 6 weeks.

2.2 Sample preparation and index determination: 24 hours after the last administration, blood was collected from the eyeballs of mice; after dislocation for execution, the liver was removed, cleaned and ground at low temperature to prepare 10% tissue homogenate, which was centrifuged at 3500 rpm and 4° C. for 10 min, and supernatant was taken and stored at −20° C. The content of MDA in the liver tissue was determined by colorimetry, and the activity of SOD in serum was determined by ELISA.

2.3 Statistical analysis: the results were expressed as x±s. The results were analyzed by One-way ANOVA Dunnett test using SPSS 20 software.

3 Results 3.1 Results: after the aging model mice induced by D-galactose were administrated, the mice had diet normally and the body weight was not changed abnormally. The serum SOD level and liver MDA content of mice in each experimental group were measured. The results are as shown in Table 1. The results show that the serum SOD activity of the mice in the model group was significantly ($P<0.01$) lower than that in the normal group, and the liver MDA content was significantly ($P<0.05$) higher than that in the normal group, indicating successful modeling. Compared with the model group, the serum SOD activity of the mice in the administration group of Compound 1 is significantly ($P<0.05$) increased, and the liver MDA content is significantly ($P<0.05$) decreased; the serum SOD activity of the mice in the administration group of Compound 2 is significantly ($P<0.05$) increased, and the liver MDA content is significantly ($P<0.05$) decreased; the serum SOD activity of the mice in the administration group of Compound 3 is significantly ($P<0.05$) higher than that in the model group, and the liver MDA content was significantly ($P<0.05$) lower than that in the model group. It indicates that Compounds 1-3 have significant antioxidant activity.

TABLE 1

Effects of Compounds 1-3 on serum SOD activity and liver MDA content in aging model mice induced by D-galactose ($\bar{x} \pm s$)

| Group | Serum SOD (U/mL) | Liver MDA (nmol/mg tissue) |
| --- | --- | --- |
| Control group | 108.57 ± 17.03[b] | 0.197 ± 0.033[a] |
| Model group | 78.70 ± 12.04 | 0.253 ± 0.081 |
| Compound 1 | 94.90 ± 8.07[a] | 0.211 ± 0.019[a] |
| Compound 2 | 97.06 ± 10.18[a] | 0.198 ± 0.037[a] |
| Compound 3 | 103.44 ± 15.75[a] | 0.183 ± 0.051[a] |

Notes:
[a]represents $P < 0.05$, [b]represents $P < 0.01$, both compared with the model group.

Comparative Example 1

For the method, refer to the method for extracting the phenolic acid glucoside compounds in Example 1. The difference lied in that only the ethanol elution concentration was changed when putting in the MCI GEL reverse phase column, the walnut ethanol extract was put in the MCI GEL reverse phase column and sequentially eluted by using deionized water, 20% ethanol, 50% ethanol and 70% ethanol, and other conditions and experimental steps were the same as those in Example 1. The results show that the elution of Compound 1 was incomplete when 20% ethanol was used, the yield was less than 60%, and it was detected in 50% ethanol, indicating that Compound 1 can be eluted completely when 30% ethanol is used.

Comparative Example 2

For the method, refer to the method for extracting the phenolic acid glucoside compounds in Example 1. The difference lied in that only the ethanol elution condition in the ODS column was changed, reduced-pressure concentration was performed, then a sample was put in an ODS column, and eluted sequentially by using deionized water, 10% ethanol and 20% ethanol solution, collection was performed, and other conditions and experimental steps were the same as those in Example 1. The results show that Compounds 2 and 3 are eluted by 10% ethanol if 5% ethanol is not used for elution first, indicating that 5% ethanol needs to be used for elution first and then 10% ethanol is used for elution.

Although the preferred examples of the disclosure have been disclosed above, they are not used to limit the disclosure. Any person familiar with the art may make various changes and modifications without departing from the spirit and scope of the disclosure. Therefore, the scope of protection of the disclosure should be defined by the claims.

What is claimed is:

1. A method for separating phenolic acid glucoside compounds from *Diaphragma juglandis Fructus*, comprising:
   crushing *Diaphragma juglandis Fructus* (DJF), adding ethanol to crushed DJF to obtain a walnut ethanol extract, loading the walnut ethanol extract onto a first reverse phase column,
   sequentially eluting the walnut ethanol extract from the first reverse phase column with deionized water, 30% ethanol, 50% ethanol, and 70% ethanol, to obtain a deionized water elution fraction and a 30% ethanol elution fraction,
   combining the deionized water elution fraction and the 30% ethanol elution fraction as a combined eluent,
   concentrating the combined eluent to obtain a concentrated combined eluent, loading the concentrated combined eluent onto second reverse phase column,
sequentially eluting the combined eluent from the second reverse phase column with deionized water, 10% ethanol, 20% ethanol, 30% ethanol, and 50% ethanol, to obtain a 10% ethanol elution fraction,
collecting the 10% ethanol elution fraction from the second reverse phase column,
concentrating the 10% ethanol elution fraction from the second reverse phase column to obtain a concentrated 10% ethanol elution fraction,
loading the concentrated 10% ethanol elution fraction onto an ODS column,
sequentially eluting the concentrated 10% ethanol elution fraction from the ODS column with deionized water, 5% ethanol solution, 10% ethanol solution, and 20% ethanol solution, to obtain an ODS eluent, and
collecting the ODS eluent, to obtain the phenolic acid glucoside compounds,
wherein the phenolic acid glucoside compounds are:
2-hydroxyl-5-methoxylphenyl-O-β-D-glucopyranoside,
6-hydroxylnaphthyl-1,2-di-O-β-D-glucopyranoside, or
2,6-dihydroxynaphthyl-O-β-D-glucopyranoside.

2. The method according to claim 1, wherein adding ethanol to crushed DJF comprises:
adding 75% ethanol to the DJF at a material-liquid ratio of 1:(10-20),
stirring for at 40° C. to 70° C. for 2 hours to 5 hours,
filtering the ethanol to obtain a supernatent,
collecting the supernatant,
repeating the adding, filtering, and collecting steps three times,
combining the supernatents,
concentrating the supernatants by removing the ethanol to obtain the walnut ethanol extract.

3. The method according to claim 1, wherein the structural formula of the 2-hydroxyl-5-methoxylphenyl-O-β-D-glucopyranoside is:

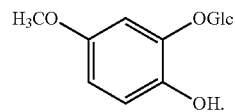

4. The method according to claim 1, wherein the structural formula of the 6-hydroxylnaphthyl-1,2-di-O-β-D-glucopyranoside is:

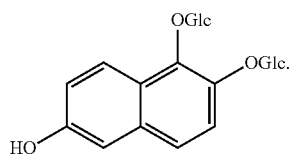

5. The method according to claim 1, wherein the structural formula of the 2,6-dihydroxynaphthyl-O-β-D-glucopyranoside is:

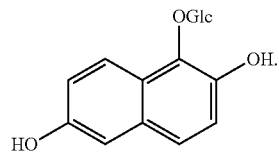

* * * * *